United States Patent [19]

Modrovich

[11] 4,372,874

[45] * Feb. 8, 1983

[54] STABILIZATION OF HYDROLYSIS PRONE LABILE ORGANIC REAGENTS IN LIQUID MEDIA

[76] Inventor: Ivan E. Modrovich, 1043 Mesa Dr., Camarillo, Calif. 93010

[*] Notice: The portion of the term of this patent subsequent to May 8, 1996, has been disclaimed.

[21] Appl. No.: 206,467

[22] Filed: Nov. 13, 1980

Related U.S. Application Data

[63] Continuation-in-part of Ser. No. 722,565, Sep. 13, 1976, abandoned, Ser. No. 764,826, Feb. 2, 1977, Pat. No. 4,153,511, Ser. No. 775,833, Mar. 9, 1977, Pat. No. 4,310,624, and Ser. No. 919,159, Jun. 26, 1978, abandoned, which is a continuation-in-part of Ser. No. 775,833, , which is a continuation-in-part of Ser. No. 764,826, , which is a continuation of Ser. No. 667,857, Mar. 17, 1976, abandoned, and a continuation-in-part of Ser. No. 722,565, Sep. 13, 1976, abandoned.

[51] Int. Cl.$^3$ .................. C12N 9/00; C09K 3/00; G01N 33/48; C12Q 1/00
[52] U.S. Cl. .......................... 436/176; 435/4; 435/11; 435/13; 435/14; 435/15; 435/16; 435/17; 435/18; 435/19; 435/23; 435/25; 435/183; 435/188; 436/17
[58] Field of Search ............ 435/4, 188, 183, 13, 435/24, 11, 21, 14, 15, 16, 17, 19, 23, 18, 25; 252/408, 194; 23/230 R, 230 B, 901, 902, 903, 904, 905, 909, 916, 918, 924, 925, 930, 931, 932

[56] References Cited

U.S. PATENT DOCUMENTS

| | | | |
|---|---|---|---|
| 2,356,890 | 8/1944 | Schulze | 252/194 |
| 3,235,089 | 2/1966 | Burroughs | 252/194 |
| 3,479,154 | 11/1969 | Cardinal | 424/1 |
| 3,519,570 | 7/1970 | McCarty | 252/135 |
| 3,539,450 | 11/1970 | Deutsch | 435/188 |
| 3,546,131 | 12/1970 | Stern et al. | 252/408 |
| 3,557,002 | 1/1971 | McCarty | 252/89 |
| 3,642,444 | 2/1972 | Guehler et al. | 252/408 |
| 3,704,806 | 12/1972 | Plachenov et al. | 252/194 |
| 3,748,272 | 7/1973 | Wenz et al. | 252/408 |
| 3,761,420 | 9/1973 | Bocardus | 252/171 |
| 3,764,478 | 10/1973 | Bergmeyer | 435/188 |
| 3,776,900 | 12/1973 | Hammer | 252/408 |
| 3,819,487 | 6/1974 | Bernt et al. | 435/188 |
| 3,853,473 | 12/1974 | Morin et al. | 252/408 |
| 3,876,375 | 4/1975 | Maurukas | 252/408 |
| 3,894,844 | 7/1975 | Pinto et al. | 252/408 |
| 3,926,735 | 12/1975 | Monte et al. | 252/408 |
| 3,986,834 | 10/1975 | Steindrink, Jr. | 252/408 |
| 4,017,420 | 4/1977 | Bowie et al. | 252/408 |
| 4,153,511 | 5/1979 | Modrovich | 435/188 |
| 4,218,536 | 8/1980 | Maurukas | 252/408 |
| 4,239,649 | 12/1980 | Cindler et al. | 252/408 |

FOREIGN PATENT DOCUMENTS

| | | | |
|---|---|---|---|
| 663418 | 5/1965 | Belgium | 252/194 |
| 1365651 | 2/1973 | Fed. Rep. of Germany | 435/188 |
| 2615958 | 12/1975 | Fed. Rep. of Germany | 435/188 |
| 1267604 | 9/1964 | France | 435/188 |
| 7603588 | 10/1976 | Netherlands | 435/188 |
| 1027430 | 4/1966 | United Kingdom | 252/194 |

OTHER PUBLICATIONS

Gallati, V. A., J. Clin. Chem. Clin. Biochem, vol. 14, No. 1, pp. 9–13 (Jan. 1976).
Doumas, B. T., et al., Clin. Chem., vol. 19, No. 9, pp. 984–993 (1973).
Eastman Organic Chemicals, Catalog No. 47, pp. 136, 154, Eastman Kodak Co., Rochester, N. Y. (May 1974).

Primary Examiner—Teddy S. Gron
Attorney, Agent, or Firm—Christie, Parker & Hale

[57] ABSTRACT

A labile, organic reagent, which is unstable in aqueous media and stable in a nonaqueous media, is stabilized by dissolving the organic reagent in a water-miscible, organic solvent which is liquid at room temperature and which is nondegradatively reactive with the organic reagent to form a solution of the organic reagent in the organic solvent. At least 1% of an inert, high-surface area particulate desiccant is added to the solution for entrapping water with the desiccant so that the residual water content of the solution is below about 0.5%. The desiccant can be removed from the solution before sealing it. More than one organic reagent can be added to the solvent, and a solubilizing agent for the organic reagent can be used.

48 Claims, No Drawings

STABILIZATION OF HYDROLYSIS PRONE LABILE ORGANIC REAGENTS IN LIQUID MEDIA

CROSS-REFERENCE TO RELATED APPLICATIONS

This application is a continuation-in-part of U.S. patent applications Ser. Nos. 722,565 filed on Sept. 13, 1976, now abandoned; 764,826 filed on Feb. 2, 1977, now U.S. Pat. No. 4,153,511, issued on May 8, 1979; 775,833 filed on Mar. 9, 1977, now U.S. Pat. No. 4,310,624; and 919,159 filed on June 26, 1978, now abandoned. The '159 application is a continuation-in-part of the '833 application; the '833 application is a continuation-in-part of the '826 application; which is a continuation of U.S. patent application Ser. No. 667,857 filed on Mar. 17, 1976 and a continuation-in-part of U.S. patent application Ser. No. 722,565 filed Sept. 13, 1976, now abandoned. The entire disclosures of each of these five patent applications are incorporated herein by these references.

BACKGROUND OF THE INVENTION

This invention relates to a new and useful method for stabilizing labile organic reagents which are prone to hydrolysis in aqueous media and which are stable in organic media. This includes coenzymes and other organic compounds, but excludes enzymes because they denature in 100% organic solvents. The organic reagents can be of biological origin or can be synthesized.

It has been estimated that 25% of all in vitro diagnostic tests conducted annually in the United States are not reliable. Unreliable tests can result in unnecessary medical treatment, the withholding of necessary treatment and lost income. Because of their high specificity, the use of enzyme determinations has significantly increased during the last few years, and indications are that this trend will continue. However, rigorous quality control measures are required to assure the accuracy and consistency of results. This requirement stems from the fact that the exact nature of enzymes, as well as the mechanisms of their action, remain unknown for the most part.

At present, the most important reason for the unreliability of in vitro diagnostic tests is the instability of the aqueous solution of the organic reagents used. Current methodologies require the use of numerous labile reagents. Due to this problem, rigorous quality control in the manufacture of in vitro diagnostic kits is required, and this quality control is, of course, costly. Moreover, if control in any step in the process is not maintained within a high degree of control standards, the quality of the final product can be reduced materially.

The present commercial state-of-the-art used for stabilizing the reactive ability of coenzymes and other organic reagents is by locking them into a solid matrix by: (a) freeze drying; (b) dry blending such as used for tableting dried powders in the pharmaceutical industries; or (c) by chemical immobilization of the reagent. Contrary to the sophistication these terms imply, these approaches are impractical and expensive. A manufacturer is forced to remove the water and supply a partial product, thus relinquishing part of the quality control cycle to the user who must dilute the final product. Laboratories are forced to pay the high cost of freeze drying and dry blending, and much reagent is wasted due to poor dilution techniques by unsophisticated laboratory personnel. Furthermore, only limited packaging modes and sizes are available.

Therefore, there is a need for a method for stabilizing labile, hydrolysis prone organic reagents in a liquid media so the reagents can be provided in a single container with excellent shelf life, where the container can be repeatedly opened for use without substantial degradation of the organic reagent therein. The method for stabilizing the labile organic reagents in a liquid media must be able to be effected with relatively low-cost, commercially available stabilizing ingredients, and the method must be effective for stabilizing the reagents in the presence of other labile reagents.

SUMMARY OF THE INVENTION

The method herein relates to stabilization of a labile organic reagent which is unstable in aqueous media and stable in nonaqueous media. According to this method, at least one such organic reagent is dissolved in a water miscible organic solvent which is nondegradatively reactive with the organic reagent and which is liquid at room temperature, and preferably at refrigerator temperature. A solution of the organic reagent in the organic solvent is thus formed. At least 1% by weight of inert, high surface area, particulate desiccant is added to the solvent for entrapping water so that the residual water content of the solution is below about 0.5% by weight, and preferably below about 0.1% by weight.

The method herein can be practiced by dissolving at least one organic reagent selected from the group consisting of adenosine monophosphate, adenosine diphosphate, adenosine triphosphate, phosphoadenylic acid sulfate, adenosylmethionine, uridine diphosphate, cytidine diphosphate, coenzyme A, tetrahydrofolic acid, biotin, thiamine pyrophosphate, pryidoxal phosphate, nicotinamide mononucleotide, cell haemin, $B_{12}$ coenzyme, NADP, NADPH, purine nucleotides, pyrimidine nucleotides, cholesterol, magnesium thymolphthalein monophosphate, dithioerythritol, dithiothreitol, N-acetyl cysteine, glutathione, mercaptoethanol, o-cresolphthalein complexone, N-acetyl cystine, gamma-glutamyl-p-nitroanilide, paranitrophenyl phosphate, phenolphthalein monophosphate, glycerol phosphate, p-nitroanilide, p-nitrophenol, ascorbic acid, tetraphenylboron, phosphoenol pyruvate, B-NAD and hydrated $NADH_2$, in a water miscible organic solvent which is liquid at room temperature and which is nondegradatively reactive with such organic reagent to form a solution of such organic reagent in the organic solvent; adding at least 1% by weight of an inert, high surface area, particulate desiccant, to the solvent either before or after dissolving the reagent in the solvent for entrapping water with the desiccant to provide a residual water content in the solution below about 0.5% by weight; and sealing the solution.

The desiccant can be added to the solvent either before or after dissolving the reagent in the solvent. The solution can be packaged with the desiccant therein, or the desiccant can be removed from the solution before packaging. Preferably the desiccant is left in the solution to avoid hydrolysis of the organic reagent when the package containing the solution is repeatedly opened and closed during use.

More than one organic reagent can be added to the solvent and, if desired, a solubilizing agent for the reagent can be used. For example, gamma-glutamyl paranitroanilide (GGP), a polar organic reagent is stabilized in water-free dimethyl sulfoxide, or in a preferred solvent mixture of water-free dimethyl sulfoxide (70% v/v) and water-free acetone (30% v/v). Solid boric acid is added to increase the solubility of the reagent in the solvent mixture, preferably before the reagent is added to the solvent mixture, and finally molecular sieves (Mesh 4A, Linde Division of Union Carbide) are added to the solution to serve as the inert desiccant. The solution can then be used for the diagnostic determination of the physiologically important enzyme gamma-glutamyl-transpeptidase in biological body fluids such as human serum or plasma. The reagent is effectively stabilized at refrigerator temperature (2°–8° C.) for several years as opposed to only several days of maximum stability of the reagent in aqueous solution under identical storage conditions.

According to the present invention, hydrolysis prone labile reagents are effectively "stabilized" in an organic solvent solution by preventing hydrolysis and decomposition of the reagent. This means of stabilization ensures long-term stability in a liquid media. Moreover, close tolerance control in manufacturing can be achieved. The resultant high quality product eliminates the inconvenience of the rigid package size and the high cost of packaging and freeze-drying and reagent waste characteristic of prior art products.

These and other features, aspects and advantages of the present invention will become better understood with reference to the following detailed description of the invention and appended claims.

DETAILED DESCRIPTION

Organic reagents which are unstable in aqueous media and stable in a nonaqueous media are stabilized for long periods of time by dissolving them in a water-miscible, organic solvent and adding a high surface area, inert particulate desiccant to the solvent to reduce the residual water content of the solution to below about 0.5% by weight, and preferably below about 0.1% by weight. The long-term stability realized by this technique occurs because the major causes of degradation of the organic reagent are eliminated.

Many organic reagents used in biological determinations are labile and degrade rapidly in aqueous solutions. This degradation is mainly the result of three major factors: (1) hydrolysis; (2) microbial action; and (3) decomposition. Removal of water greatly reduces or completely eliminates degradation stemming from these factors.

As already discussed, at present, water is removed from the media preparations in clinical diagnostic products via the technique called freeze-drying or lyophilization. Lyophilization is accomplished by preparing the product in question in an aqueous media, freezing and evaporating the water from the media under vacuum and sealing the container. Another state-of-the-art method is to use the dry ingredients directly, add inert ingredients and dry blend the mix. At the time of use the dry material, both freeze-dried and dry-blended, is dissolved in water and must be used within days to assure efficacy.

By contrast, according to the present invention, preservation of labile organic reagents is effected in organic solvent media by eliminating aqueous degradation.

This method is useful for stabilization of a wide variety of organic reagents, including but not limited to coenzymes. Coenzymes are lower molecular weight organic chemicals of well-defined structure, whose reactions or interactions are necessary for specific enzyme assays or reactions. Coenzymes are very useful in clinical assay procedures. Some have strong absorbance, and their reactions are stoichiometric with the substrate. Therefore, the creation or disappearance of absorbing form of the coenzyme can be followed photometrically. Nicotinamide-adenine dinucleotide (NAD) and its reduced form ($NADH_2$) are used in many important clinical assays. NAD and $NADH_2$ and their salts have a molecular weight of about 700 and are very complex organic molecules. $NADH_2$ absorbs strongly at 340 nm whereas NAD does not adsorb at this wavelength.

$NADH_2$ is extremely unstable in water solution or in dry form when exposed to humid environments, even when frozen $NADH_2$ must be kept free of moisture. Stability is better at alkaline pH, whereas at acid pH $NADH_2$ decomposes very rapidly in a matter of minutes. Neither the exact mechanism, nor the end products are of significance except that decomposed $NADH_2$ can no longer effectively function as a coenzyme nor does it possess the extinction coefficient at 340 nm. The typical commercial form is a dry desiccated package or it is freeze dried and stored under nitrogen.

Examples of other coenzymes and examples of nucleotides which can be stabilized according to the present invention are adenosine monophosphate, adenosine diphosphate, adenosine triphosphate, phosphoadenylic acid sulfate, adenosylmethionine, uridine diphosphate, cytidine diphosphate, coenzyme A, tetrahydrofolic acid, biotin, thiamine pyrophosphate, pyridoxal phosphate, nicotinamide mononucleotide, flavine mononucleotide, flavine-adenine dinucleotide, cell haemin, and $B_{12}$ coenzyme. The method also applies to nicotinamideadenine dinucleotide phosphate in reduced (NADPH) or oxidized (NADP) form, as well as purine or pyrimidine nucleotides.

Other organic reagents for which this technique can be used include cholesterol, magnesium thymolphthalein monophosphate, dithioerythritol, dithiothreitol, N-acetyl cysteine, glutathione, mercaptoethanol, o-cresolphthalein complexone, N-acetyl cystine and adenosine triphosphate. A mixture of organic reagents can also be used.

In the clinical diagnostic field, the commercial application of the present invention is represented by, but not limited to, the diagnostic reagents used to determine enzyme activity as, for example, gamma glutamyl transpeptidase (gamma-GT) activity, in biological fluids, and the like. Compositions prepared in accordance with the present invention can be used to determine and quantitate the activity of other enzymes of the composition may be used as standard material in the determination. Some examples of uses are listed below:

(a) stabilization of gamma-glutamyl-p-nitroanilide (gamma-GPNA) to be used as substrate for the determination of the enzyme gamma glutamyl transpeptidase (gamma-GT) activity;

(b) stabilization of paranitrophenylphosphate (PNP) to be used as substrate for the determination of alkaline (ALP) and acid phosphatase (ACP) activity;

(c) stabilization of phenophthalein monophosphate (PMP) for the determination of alkaline phosphatase activity;

(d) stabilization of glycerol phosphate for ALP determination;

(e) stabilization of p-nitroanilide and p-nitrophenol to standardize the determinations in Nos. (a) and (b) above;

(f) stabilization of ascorbic acid to be used as standard material in the quantitative determination of the same in biological fluids;

(g) stabilization of tetraphenylboron used in the quantitative determination of potassium in biological fluids;

(h) stabilization of ascorbic acid to be used as a reducing solution;

(i) stabilization of bilirubin (a bile acid) to be used as a standard solution for the determination of the same in biological fluids; and (j) stabilization of phosphoenol pyruvate to be used as a substrate for the enzyme phosphokinase.

In general, the organic reagent is dissolved in a substantially water-free, but water-miscible organic solvent resulting in a highly concentrated homogeneous solution. The solvent is chosen based on its solvolytic properties with respect to the solute. For example, a polar compound such as ascorbic acid is dissolved in a polar, water-miscible organic solvent such as dimethyl sulfoxide. On the other hand, ethanol is used for the preservation of glycerol phosphate, which is relatively nonpolar and contains several hydroxyl groups.

For dissolving $NADH_2$ and other organic reagents, relatively inert organic solvents of neutral or alkaline pH are preferred. Such inert organic solvents include alcohols. Especially preferred are liquid polyols containing from 2 to 4 hydroxyl groups and 2 to 10 carbon atoms. Examples of such preferred polyols are glycerol, ethylene glycol, propylene glycol or butanediol. Propylene glycol, 1,2-propanediol, was found to be the solvent of choice for $NADH_2$ and hydrated $NADH_2$. The pH of an organic solvent can be determined by mixing the solvent with water and measuring the pH of the mixture.

In preparing the stable "liquid" solution of any aqueous, labile compound, the organic solvent of choice is a major consideration. As used herein, the term "solvent" refers to a single solvent or a mixture of two or more solvents. The proper organic solvent or solvent mixture requires at least the following properties:

(a) it dissolves the reagent in question;
(b) it is nondegradatively reactive with the reagent (free energy of solvolysis is low, i.e., normal resonance is established);
(c) it is a liquid at least at room temperatures, and preferably also at refrigerator temperatures; and
(d) it does not interfere or does so negligibly with the intended use of the reagent.

As used herein, the term "nondegradatively reactive" means that a solvent or a desiccant or a solubilizing agent does not react with or affect the organic reagent in such a way that the effectiveness of the reagent is impaired.

The second major consideration is the desiccant of choice. The proper desiccant is one that has at least the following properties:

(a) it removes water from the solvent mixture;
(b) it is nondegradatively reactive with the reagent or reagents used;
(c) it continues to remove water from the solution as water is introduced, such as by repeated opening and closure of the container; and
(d) it does not interfere with the intended use of the reagent.

The desiccant maintains the desired low water content, i.e., below 0.5%, preferably below 0.1%. The desiccant must be an efficient water absorber substantially nonreactive with the organic reagent, and of neutral or alkaline pH when stabilizing $NADH_2$. The desiccant is preferably a high area hydroscopic agent such as a natural or synthetic molecular sieve having a particle size from 2 to 16 mesh present in an amount of at least 1% v/v, typically from 5 to 20% v/v. The amount of surface area is important since the material acts to absorb water into its pores.

Molecular sieves are zeolites or similar materials whose atoms are arranged in a crystal lattice in such a way that there are a large number of small cavities interconnected by smaller openings or pores of precisely uniform size. Normally, these cavities contain water molecules, but, upon heating under a vacuum, this water is driven off without any change in the remaining crystal lattice. The network of cavities and pores can occupy 50% of the total volume of the crystals. Molecular sieves have a strong tendency to reabsorb water and other small molecular weight liquids.

A few natural zeolites exhibit molecular sieve characteristics to a limited degree. Synthetic zeolites are available in several sizes having pore openings of 3, 4, 5 and 10 angstrom units in diameter with high capacity for absorption and regeneration even when used at elevated temperatures.

It has been found in connection with the present invention that after the composition has been stabilized in the presence of the organic solvent as well as the inert particulate desiccant, the desiccant can be removed without otherwise materially affecting the stability of the composition. Generally, it has been found that the composition should be stored for a period of at least about 24 hours at room temperature in the presence of the desiccant. During this time, any traces of water are absorbed by the desiccant and, upon removal of the same, there is essentially no water available in the composition. The composition may also be opened on a limited basis and even though water in the air may enter the upper end of the container, the amount of water is relatively small so that it does not cause any material decomposition of the labile components in the composition.

Generally, the desiccant should be kept in contact with the stabilized solution for a period which depends upon the amount of water which was initially in the solution at the time of preparation. In many cases it has been found that the desiccant should remain in contact with the solution for about three to four days. This time can be shortened by heating the composition at least to the point where no decomposition of the labile components will occur. Thus, it has been found that it is possible to heat the compositions to about a 60° C. temperature without affecting the labile components. The important factor is that the desiccant should remain in the solution until there is no more than about 0.5% v/v of water.

In the aforementioned parent application, Ser. No. 667,857, filed Mar. 17, 1976, it was deemed necessary to maintain the desiccant along with the organic solvent in the composition in order to maintain stability. Although this is a preferred embodiment of this invention, it has been subsequently found that stability of the composition is not materially decreased even when the desiccant has been removed after the initial stage of stability has been attained.

An advantage of removal of the desiccant from the stabilized solution is improved precision in dispensing solution because the desiccant would otherwise absorb some of the solvent itself, or at least maintain a portion of the solvent on the surface of the desiccant by surface tension. By removing the desiccant, it is possible to dispense precise amounts in those cases where quantization of the solution is a critical or important factor.

For example, it can be observed that the coefficient of expansion of some solvents, such as propylene glycol, is temperature dependent. The amount of the solution which can be dispensed into a container can be very careful controlled at the manufacturing site, but is not easily controlled in the field during use.

A third major consideration is the solubilizing agent to use, if any, to increase the solubility of the reagent in question to desired levels. The minimum requirements of a solubilizing agent are:

(a) it increases the solubility of the reagent in question (usually by forming a solvated complex with the organic solvent which then is a better solvent for the reagent);

(b) it is nonreactive or nondegradatively reactive with the reagent; and (c) it does not interfere, or does negligibly, with the intended use of the organic reagent.

Examples of suitable solubilizing agents for many organic reagents are boric acid, imidazole, salycilate, ascorbic acid and combinations thereof.

The order of addition of solvents, reagents, solubilizing agents is, in general, unimportant, but for practical purposes it is preferred to first add and dissolve the solubilizing agent in the solvent, followed by the addition of the aqueous, labile organic reagents. The reagent is then dissolved by stirring and/or application of heat if necessary, but usually so that the temperature of the solvent mixture does not exceed 50° C. or the boiling point of the solution, whichever is lower. This is followed by filtering the solution to remove any debris or undissolved matter and storing the filtered solution over the desiccant in a tightly-capped, water-tight container.

At time of use, the solution is mixed with aqueous buffers which contain one or more other reactive ingredients, and the resulting solution is used in the same manner as a dry blend or a reconstituted freeze-dried preparation would be used. This technique eliminates the high cost of freeze-drying the labile reagents from an aqueous reaction mixture and then reconstituting the reagent just prior to use. By so doing, this method allows flexibility in packaging and application, and insures product quality. Providing a water-based reaction mixture along with the stabilized labile solution, provides and insures the quality of all components of the product for the clinical diagnostic determination in question.

Exemplary of stabilization of the labile organic reagents is stabilization of gamma-glutamyl-p-nitroanilide (gamma-GPNA). This is accomplished by dissolving the gamma-GPNA in an organic solvent, such as dimethyl sulfoxide, containing no more than 0.5% water on a v/v basis. Thereafter, a solid desiccant is added to fully remove the water (below 0.01% v/v). A solubilizing agent, such as boric acid, imidazole, salycilate, and the like, can be used if necessary. The solubilizing agent not only serves as a solubilizer, but as a stablizer as well. Preferably, the solubilizing agent is added to the solvent before the organic reagent is added to the solvent. Thereafter, the solution is filtered and stored in an inert container over desiccant and tightly closed.

In accordance with the present invention, more than one reagent can be stabilized in this solution. In this case, the other reagent could be added prior to or after the additon of gamma-GPNA. For example, in an embodiment of the present invention, paranitrophenyl phosphate (PNPP) can be added as the other compound.

After the dissolution of the compounds another waterfree solvent such as acetone may also be added. This allows the storage of the solution at 2° to 8° C. without solidifying (dimethyl sulfoxide solution solidifies at 10° to 18° C.). Storage at low temperatures significantly increases shelf-life.

After the liquid stabilized solution is prepared, it is then dispensed into glass or high density polyethylene bottles containing molecular sieves, which are sealed in an airtight condition. These bottles are typically stored under refrigeration. The projected shelf life of the stabilized organic reagents is up to four years under these conditions without appreciable degradation.

Labile organic reagents treated according to this invention have many advantages. For example, long-term stability without any substantial effect on enzymatic reactivity or photometric absorptivity is realized. The invention provides reagents where quality control is assured throughout manufacturing, packaging, storage, and use. The inconvenience of limited package sizes of prior art reagents is eliminated as is the high cost of packing, freeze-drying, and reagent waste. The liquid reagent systems provide flexibility in use because separation of ingredients is easily accomplished. The liquid system offers better reagent homogeneity and packaging, as well as flexibility in usage, compared to the freeze-dried or dry media preparations.

Stabilized organic reagents of the invention have been compared against fresh aqueous organic reagents. The studies show that aged stabilized reagents of the present invention and fresh aqueous reagents have comparable accuracy, sensitivity, and precision.

In diagnostic enzymology, the stabilization of organic reagents in a ready-to-use liquid media is a new and exciting approach to satisfy the needs of the clinical laboratory and the reliability demands of regulatory authorities. The flexibility of liquid organic reagents systems ensures their applicability to automated instrumentation, as well as their convenience in manual testings.

Furthermore, the solvent system used can provide for stabilization of more than one reagent in the same liquid organic media. Another advantage of the present invention is that the organic reagents exhibit good solubility (i.e., miscible) in aqueous buffers.

A further advantage of the present invention is that more than one organic reagent can be stabilized with the same solution. These and other advantages of the present invention will become better understood with reference to the following examples.

EXAMPLE 1

Ten grams of boric acid were added to 100 milliliters of dry dimethyl sulfoxide in a glass beaker. The beaker was covered immediately with parafilm, and the boric acid was dissolved by stirring at room temperature. Thereafter, 4.3 grams of gamma glutamyl-p-nitroanilide were added to the mixture and the gamma-GPN was dissolved by additional stirring. The solution so obtained was filtered through filter paper, and the filtered solution was stored over dry molecular sieves (zeolites, Linde Division, Union Carbide Corporation). Approximately 30 beads of molecular sieves, size mesh 4A (4 to 8 mm in diameter) were added for each 10 ml of the solution. The solution was stored in a tightly capped amber glass bottle over the molecular sieves. The solution can be dispensed into smaller amber glass bottles in any quantity size containing approximately 30 beads of mesh 4A molecular sieves per 10 ml of solution, where the bottles are maintained tightly capped. The sample was stored at room temperature for a year without significant degradation.

EXAMPLE 2

The procedure of Example 1 was repeated in every essential detail with the exception that a mixture of 30% (v/v) acetone and 70% (v/v) dimethyl sulfoxide was used instead of dimethyl sulfoxide in Example 1. The sample was stored under refrigeration at 2° to 8° C. Storage stability is believed to be up to four years without significant degradation. The addition of acetone prevents the freezing of the mixture under refrigeration temperature.

EXAMPLE 3

Thirty microliters of the solution prepared by the method of Example 1 or Example 2 were added for each milliliter of 0.4 molar aqueous tris (hydroxymethyl)-aminomethane buffer solution, pH 8.2 ±0.15, containing 160 mM glycyl glycine. The resulting solution was used for the determination of gamma-GT activity in biological fluids. The procedure for the determination of gamma-GT activity can be performed as follows: to 2.9 ml of the above solution, 100 microliters of human serum sample are added, mixed, and the rate of formation of paranitroaniline (PNA) is followed at 405 nm at constant temperature, such as 37° C. The rate of formation of the paranitroaniline is directly proportional to the activity (concentration) of the diagnostically important liver enzyme gamma-glutamyltranspeptidase (gamma-GT). The reaction scheme involved is as follows:

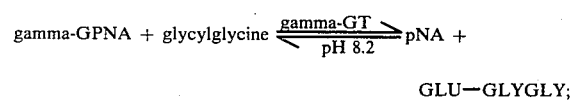

gamma-GPNA + glycylglycine $\underset{pH\ 8.2}{\overset{gamma\text{-}GT}{\rightleftharpoons}}$ pNA + GLU—GLYGLY;

pNA strongly absorbs at 405 nm, whereas gamma-GPNA does not.

In each of the following examples, organic reagent is dissolved in a solvent. Each of the solutions formed in the following examples can be stabilized for long-term storage by the addition of a desiccant in accordance with principles of the present invention and as disclosed in Examples 1 and 2.

EXAMPLE 4

CHOLESTEROL STANDARD—300 mg%

Six hundred mg of cholesterol ($C_{27}H_{45}OH$), Mp. 148° to 149° C., were dissolved in 20 ml water-free tetrahydrofuran (Bp 66° to 67° C., $H_2O \leq 0.01\%$, J. T. Baker Chemical Company, Phillipsburg, New Jersey 08865). The solution was diluted to 100 ml with water-free ($\leq 0.01\%$) dimethyl sulfoxide (($CH_3)_2SO$, available from any major chemical distributor).

Sebesquently, 0.5 to 2.5 ml of a non-ionic surfactant, such as Triton X-100, a trademark of Rohm & Haas Company and commercially available from J. T. Baker Chemical Company, Phillipsburg, New Jersey 08865, were added and the resulting solution was diluted to 200.0 ml with isopropanol.

The solution was thoroughly mixed and can be used to standardize commonly used cholesterol methods for the determination of cholesterol in biological fluids, i.e., either the Lieberman-Burchard reaction based methodologies or the state-of-the-art enzymatic methods as described in Bergmeyer, *Methods of Enzymatic Analysis,* 4:1890–93, 2nd ed, Academic Press.

It is understood that by using the above method, standard cholesterol solutions of any desired concentration level can be prepared or standardization can be accomplished by using varying amounts of a single standard cholesterol solution as the sample for an assay.

EXAMPLE 5

Substrate Solution 4.0 g solid magnesium thymolphthalein monophosphate were dissolved in 30 ml liquefied phenol (J. T. Baker Chemical Company, Phillipsburg, N. J. 08865) and the solution was diluted to 100 ml with methanol. The solution was heated to 60° C. to facilitate dissolution of the solid. The solution is believed to be stable at 25° C. for 18 months to two years without substantial hydrolysis if packaged with a desiccant.

Using the above solution, the determination of alkaline phosphatase can be performed as follows: To 2.5 ml of 0.2 M (pH 10.0) 2-amino-2-methyl-1-propanol buffer, 2 drops (75 microliters) of the solution are added and mixed. This solution is prewarmed to 37° C. in a water bath or heating block and 100 microliters of biological fluid sample are added. This mix is incubated at 37° C. for 10 minutes and 1 ml of 0.5 N sodium hydroxide, 2.2% sodium carbonate solution are added and mixed. The resulting color is read at 595 nm. The enzyme activity is read from a standard curve prepared from pure thymolphthalein according to the enzyme activity unit definition preferred.

EXAMPLE 6

4.0 G magnesium thymolphthalein monophosphate were dissolved in 100 ml of water-free dimethyl sulfoxide. This solution can be used according to Example 5.

EXAMPLE 7

Sulfhydryl Compounds

A. Dithiothreitol was dissolved in water-free 1,2-propanediol at desired concentration levels. This soulution protects (stability two years at 4° to 8° C.) the sulfhydryl groups from oxidation. The solution was bottled and capped for storage.

Uses: The solution can be used, but is not limited in use, in the diagnostic determination of the exzyme creatine phosphokinase in biological fluids according to the method of J. T. Oliver, *Biochem. J.,* 61:116 (1955). The sulfhydryl solution is added to the CPK (creatine phosphokinase) reagent mix prior to assay in such a manner that the final glycol concentration does not exceed 10% v/v in the CPK reagent mix.

B. Dithioerythritol can be substituted for dithioerythreitol in the method of Example 7A.

C. N-acetyl cysteine can be substituted for dithiothreitol in the method of Example 7A.

D. Glutathione can be substituted for dithiothreitol in the method of Example 7A.

E. Mercaptoethanol can be substituted for dithiothreitol in the method of Example 7A.

F. Water-free glycerol can be substituted for 1,2-propanediol in the method of Example 7A.

G. Water-free methanol can be substituted for 1,2-propanediol in the method of Example 7A.

H. Water-free ethanol can be substituted for 1,2-propanediol in the method of Example 7A.

EXAMPLE 8

Bilirubin Standard—20 mg%

20.0 mg bilirubin (ICN.K & K Laboratories, Plainview, New York) were dissolved in 100 ml water-free dimethyl sulfoxide. The solution was stored in tightly sealed amber glass bottles at 4° to 8° C. in dark. The solution is believed to be stable for 12 to 18 months when stored and prepared according to this invention. This solution can be used as a primary standard in the standardization of bilirubin assay in biological fluids, such as in the method of Malloy and Evelyn (Malloy, H. T., Evelyn, K. A., *J. Biological Chemistry*, 119:481 (1937). It is understood that according to this example, bilirubin standards of any concentration level desired can be prepared, and a single standard of varying aliquots can be used for standardization purposes as desired.

EXAMPLE 9

The organic solvent mixture of 30% liquefied phenol-70% methanol was used instead of dimethyl sulfoxide in the method of Example 8.

EXAMPLE 10

Calcium Indicator—0.167% w/v

One hundred sixty-seven mg o-cresolphthalein complexone (Metalphtalein 1, ICN.K & K Laboratories, Plainview, New York, Catalog No. 1367) were dissolved in 100 ml water-free dimethyl sulfoxide. Approximately 400 beads of molecular sieves (Mesh 4A, Linde Division, Union Carbide Corporation) were added and stored tightly capped in an amber glass bottle. It is believed that this solution is stable for 12 to 18 months at 25° C. when prepared and stored as directed.

Uses: To each milliliter buffer reagent (3% w/v 2-ethylaminoethanol in water containing 0.2% 8-hydroxyquinoline) 1 drop (approximately 30 microliters) of the calcium indicator solution prepared as described above is added. After mixing, this mixture is used for the assay of calcium levels in biological fluids. The mixture should be used within 60 minutes of preparation by adding 50 microliters sample to 4 ml mixture aliquots and by reading final absorbances five minutes later at 565 nm on a properly calibrated spectrophotometer.

EXAMPLE 11

A solvent mixture of 30% v/v liquefied phenol and 70% v/v methanol was substituted for dimethyl sulfoxide of Example 10.

EXAMPLE 12

Phosphorylating Agent

A. Phosphenolpyruvate (monocyclohexylammonium salt thereof) was dissolved in water-free dimethyl sulfoxide at desired concentration levels. Twenty to 40 beads of molecular sieves (Mesh 4A, Linde Division, Union Carbide Corporation) were added for each 10 ml of solution. The solution was stored in amber glass bottles tightly capped at 4° to 8° C. The solution is believed to be stable for 12 to 18 months.

The solution can be used as a phosphorylating agent, such as in the method of Tanzer and Gilvarg (Tanzer, M. L., and Gilvarg, C., *J. Biological Chemistry*, 234:3201 (1959). Dimethyl sulfoxide levels of less thant 5% v/v in the final reaction mixture of Tanzer and Gilvarg cause negligible enzymatic inhibition.

B. A solvent mixture of 30% v/v acetone and 70% v/v dimethyl sulfoxide can be substituted for the dimethyl sulfoxide of Example 12A.

C. A solvent mixture of 50% v/v methanol and 50% v/v liquefied phenol can be substituted for dimethyl sulfoxide of Example 12A.

EXAMPLE 13

Oxidized Coenzyme Solution

A. Ten g of β-nicotinamide adenine dinucleotide (lithium salt thereof ($C_{12}H_{26}N_7O_{14}P_2Li.2H_2O$) Boehringer Mannheim Biochemicals, Indianapolis, Indiana) were dissolved in 100 ml of water-free ethylene glycol. The solution is believed to be stable at 25° C. for 6 to 12 months and at 4° to 8° C. for two to four years, when stored in an amber glass bottle tightly capped. Solid desiccant such as molecular sieves can be added to remove water trapped from the atmosphere when the bottle is repeatedly opened and closed during use. Some examples of uses are as follows:

(1) Use as a coenzyme in the determination of lactic dehydrogenase activity in biological fluids (Wroblewski, F., and La Due, J. S., *Pro. Soc. Exp. Biol. Med.*, 90:210 (1955); and (2) Use as a coenzyme in the determination of CPK enzyme activity in biological fluids (Oliver, I. T., *Biochem, J.*, 61:116 (1955); Rosalki, S. B., *J. Lab. Clin. Med.*, 60:695 (1967).

B. A solvent mixture of 30% v/v water-free ethanol and 70% v/v ethylene glycol was used instead of ethylene glycol of Example 13A.

C. Free acid can be used instead of the lithium salt of Examples 13A or 13B.

D. Sodium salt can be used instead of the lithium salt in Examples 13A and 13B.

E. NADP instead of NAD can be used in Examples 13A–13D.

EXAMPLE 14

Ascorbic Acid Solution 10.0 g of L-ascorbic acid were dissolved in 100 ml of water-free dimethyl sulfoxide. The solution was stored in tightly capped glass containers. The solution can preserve L-ascorbic acid at 25° C. in excess of five years according to accelerated aging tests. L-ascorbic acid solutions of any desired concentration can be prepared either as the primary standard solution or as reducing solutions.

Although this invention has been described in considerable detail with reference to certain versions thereof, other versions are possible. Therefore, the spirit and scope of the appended claims should not be limited to the description of the preferred versions contained herein.

I claim:

1. A method for stabilizing a labile organic reagent which is unstable in aqueous media and stable in nonaqueous media, comprising in combination the steps of:
   (a) dissolving at least one organic reagent selected from the group consisting of adenosine monophosphate, adenosine diphsophate, adenosine triphosphate, phosphoadenylic acid sulfate, adenosylmethionine, uridine diphosphate, cytidine diphosphate, coenzyme A, tetrahydrofolic acid, biotin, thiamine pyrophosphate, pryidoxal phosphate, nicotinamide mononucleotide, cell haemin, $B_{12}$ coenzyme, NADP, NADPH, purine nucleotides, pyrimidine nucleotides, cholesterol, magnesium thymolphthalein monophosphate, dithioerythritol, dithiothreitol, N-acetyl cysteine, glutathione, mercaptoethanol, o-cresolphthalein complexone, N-acetyl cystine, gamma glutamyl-p-nitroanilide, bilirubin, paranitrophenyl phosphate, phenolphthalein monophosphate, glycerol phosphate, p-nitroanilide, p-nitrophenol, ascorbic acid, tetraphenylboron, phosphoenol pyruvate, B-NAD and hydrated $NADH_2$, in a water miscible organic solvent which is liquid at room temperature and which is nondegradatively reactive with such organic reagent to form a solution of such organic reagent in the organic solvent; and
   (b) providing in contact with the solution at least one percent by weight of an inert, high surface area, particulate desiccant for entrapping water to provide a residual water content in the solution below about 0.5% by weight; and
   (c) sealing the solution.

2. The method as recited in claim 1 further comprising the step of removing substantially all of the desiccant from the solution prior to sealing the solution.

3. The method of claim 1 in which the solvent comprises a polyol containing from 2 to 4 hydroxyl groups and from 2 to 10 carbon atoms.

4. The method of claim 3 in which the solvent is a 1,2-propanediol.

5. The method of claim 1 in which the desiccant is a molecular sieve present in an amount from 5-20% v/v.

6. The method of claim 5 in which the desiccant has a particle size from about 2-16 mesh.

7. The method of claim 1 in which the organic reagent is selected from the group consisting of:
   gamma-glutamyl-p-nitroanilide
   paranitrophenyl phosphate
   phenophthalein monophosphate
   glycerol phosphate
   p-nitroanilide
   p-nitrophenol
   ascorbic acid
   tetraphenylboron
   bilirubin
   phosphoenol pyruvate
   cholesterol
   magnesium thymolphthalein monophosphate
   dithioerythritol
   dithiothreitol
   N-acetyl cysteine
   glutathione
   mercaptoethanol
   o-cresolphthalein complexone
   N-acetyl cystine
   adenosine triphosphate
   β-nicotinamide adenine dinucleotide
   NADPH
   NADP
   hydrated $NADH_2$
   adenosine monophosphate
   adenosine diphosphate
   and combinations thereof.

8. The method of claim 1 including the step of adding to the solvent a solubilizing agent for the organic reagent, wherein the solubilizing agent is nondegradatively reactive with the reagent.

9. The method of claim 8 in which the solubilizing agent is selected from the group consisting of boric acid, imidazole, salycilate, ascorbic acid, and combinations thereof.

10. The method of claim 1 in which the dissolving step comprises adding gamma glutamyl-p-nitroanilide to a solvent selected from the group consisting of dimethyl sulfoxide, acetone, and combinations thereof.

11. The method of claim 10 including the step of adding boric acid to the solvent for solubilizing the gamma glutamyl-p-nitroanilide.

12. The method of claim 1 in which the step of dissolving comprises dissolving cholesterol in a solvent comprising tetrahydrofuran, dimethyl sulfoxide, and isopropanol.

13. The method of claim 1 in which the step of dissolving comprises dissolving magnesium thymolphthalein monophosphate in a solvent comprising phenol and methanol.

14. The method of claim 1 in which the organic reagent is selected from the group consisting of dithiothreitol, dithioerythritol, N-acetyl cysteine, glutathione, mercaptoethanol, and combinations thereof, and the solvent is a polyol containing from 2 to 4 hydroxyl groups and from 4 to 10 carbon atoms.

15. The method of claim 1 in which the step of dissolving comprises dissolving o-cresolphthalein complexone in a solvent comprising dimethyl sulfoxide.

16. The method of claim 1 in which the step of dissolving comprises dissolving o-cresolphthalein complexone in a solvent comprising phenol and methanol.

17. The method of claim 1 in which the step of dissolving comprises dissolving a salt of phosphoenol pyruvate in a solvent selected from the group consisting of dimethyl sulfoxide, acetone, and combinations thereof.

18. The method of claim 17 wherein the salt of phosphoenol pyruvate is the monocyclohexylammonium salt of phosphoenol pyruvate.

19. The method of claim 1 wherein the step of dissolving comprises dissolving a salt of β-nicotinamide adenine dinucleotide in a solvent selected from the group consisting of ethanol, ethylene glycol, and combinations thereof.

20. The method of claim 1 in which the step of dissolving comprises dissolving a lithium salt ($C_{21}H_{26}N_7O_{14}Li \cdot 2H_2O$) of β-nicotinamide adenine dinucleotide phosphate in solvent.

21. The method of claim 1 in which the step of dissolving comprises dissolving ascorbic acid in dimethyl sulfoxide.

22. The method of claim 10 in which the dissolving step further comprises selecting dimethyl sulfoxide as the solvent and dissolving paranitrophenyl phosphate and gamma glutamyl-p-nitroanilide in the dimethyl sulfoxide.

23. The method of claim 11 in which the dissolving step further comprises selecting dimethyl sulfoxide as the solvent and dissolving paranitrophenyl phosphate and gamma glutamyl-p-nitroanilide in the dimethyl sulfoxide and boric acid.

24. The method as recited in claim 1 wherein the desiccant is not removed from the solution.

25. The method of claim 24 in which the solvent comprises a polyol containing from 2 to 4 hydroxyl groups and from 2 to 10 carbon atoms.

26. The method of claim 25 in which the solvent is a 1,2-propanediol.

27. The method of claim 25 in which the desiccant is a molecular sieve present in an amount from 5 to 20% v/v.

28. The method of claim 27 in which the desiccant has a particle size from about 2 to 16 mesh.

29. The method of claim 24 in which the organic reagent is selected from the group consisting of:
gamma-glutamyl-p-nitroanilide
paranitrophenyl phosphate
phenophthalein monophosphate
glycerol phosphate
p-nitroanilide
p-nitrophenol
ascorbic acid
tetraphenylboron
phosphoenol pyruvate
cholesterol
magnesium thymolphthalein monophosphate
dithioerythritol
dithiothreitol
N-acetyl cysteine
glutathione
mercaptoethanol
o-cresolphthalein complexone
N-acetyl cystine
adenosine triphosphate
$\beta$-nicotinamide adenine dinucleotide
NADPH
NADP
hydrated NADH$_2$
adenosine monophosphate
adenosine diphosphate
and combinations thereof.

30. The method of claim 24 including the step of adding to the solvent a solubilizing agent for the organic reagent, wherein the solubilizing agent is nondegradatively reactive with the reagent.

31. The method of claim 30 in which the solubilizing agent is selected from the group consisting of boric acid, imidazole, salycilate, ascorbic acid, and combinations thereof.

32. The method of claim 24 in which the step of adding gamma glutamyl-p-nitroanilide, a solvent selected from the group consisting of dimethyl sulfoxide, acetone, and combinations thereof.

33. The method of claim 32 including the step of adding boric acid to the solvent for solubilizing the reagent.

34. The method of claim 24 in which the step of dissolving comprises dissolving cholesterol in a solvent comprising tetrahydrofuran, dimethyl sulfoxide, and isopropanol.

35. The method of claim 24 in which the step of dissolving comprises dissolving magnesium thymolphthalein monophosphate in a solvent comprising phenol and methanol.

36. The method of claim 24 in which the organic reagent is selected from the group consisting of dithiothreitol, dithioerythritol, N-acetyl cysteine, glutathione, mercaptoethanol and combinations thereof, and the solvent is a polyol containing from 2 to 4 hydroxyl groups and from 4 to 10 carbon atoms.

37. The method of claim 24 in which the step of dissolving comprises dissolving o-cresolphthalein complexone in a solvent comprising dimethyl sulfoxide.

38. The method of claim 24 in which the step of dissolving comprises dissolving o-cresolphthalein complexone in a solvent comprising phenol and methanol.

39. The method of claim 24 in which the step of dissolving comprises dissolving a salt of phosphoenol pyruvate in a solvent selected from the group consisting of dimethyl sulfoxide, acetone, and combinations thereof.

40. The method of claim 39 wherein the salt of phosphoenol pyruvate is the monocyclohexylammonium salt of phosphoenol pyruvate.

41. The method of claim 24 wherein the step of dissolving comprises dissolving a salt of $\beta$-nicotinamide adenine dinucleotide in a solvent selected from the group consisting of ethanol, ethylene glycol, and combinations thereof.

42. The method of claim 24 in which the step of dissolving comprises dissolving a lithium salt $(C_{21}H_{26}N_7O_{14}Li \cdot 2H_2O)$ of $\beta$-nicotinamide adenine dinucleotide phosphate in solvent.

43. The method of claim 24 in which the step of dissolving comprises dissolving ascorbic acid in dimethyl sulfoxide.

44. The method of claim 32 in which the dissolving step further comprises selecting dimethyl sulfoxide as the solvent and dissolving paranitrophenyl phosphate and gamma glutamyl-p-nitroanilide in the dimethyl sulfoxide.

45. The method of claim 33 in which the dissolving step further comprises selecting dimethyl sulfoxide as the solvent and dissolving paranitrophenyl phosphate and gamma glutamyl-p-nitroanilide in the dimethyl sulfoxide and boric acid.

46. A product prepared by the method of claim 24 comprising the solution sealed with the desiccant.

47. A method for stabilizing a labile organic reagent which is unstable in aqueous media and stable in a nonaqueous media comprising in combination the steps of:
(a) dissolving at least one such organic reagent in a water-miscible, organic solvent which is liquid at room temperature and which is nondegradatively reactive with such organic reagent to form a solution of such organic reagent in the organic solvent; and
(b) providing in contact with the solution at least 1% by weight of an inert, high-surface area particulate desiccant for entrapping water;
(c) maintaining the desiccant in the solution for a time sufficient to reduce the residual water content of the solution to below about 0.5%; and
(d) sealing the solution.

48. A method for stabilizing a labile organic reagent which is unstable in aqueous media and stable in a nonaqueous media comprising the steps of:
(a) dissolving at least one solubilizing agent for the organic reagent in a water-miscible, organic solvent which is liquid at room temperature and which is nondegradatively reactive with the organic reagent, wherein the solubilizing agent is nondegradatively reactive with the organic reagent;

(b) adding the organic reagent to the organic solvent and stirring the solvent;
(c) filtering the solution to remove any debris or undissolved reagent or solubilizing agent;
(d) adding at least 1% by weight of an inert, high-surface area particulate desiccant, to the solution for entrapping water with the desiccant so that the residual water content of the solution is below about 0.5%; and
(e) sealing the solution.

* * * * *